(12) United States Patent
Bouchoux et al.

(10) Patent No.: US 12,246,194 B2
(45) Date of Patent: Mar. 11, 2025

(54) METHOD AND SYSTEM FOR DETECTING A FAULT IN ACOUSTIC COUPLING BETWEEN AN ULTRASONIC DEVICE AND A TISSUE TO BE TREATED

(71) Applicant: CARTHERA, Lyons (FR)

(72) Inventors: Guillaume Bouchoux, Villeurbanne (FR); Matthieu Cholvy, Peage de Roussillon (FR); Cyril Martin, Lyons (FR)

(73) Assignee: CARTHERA, Lyons (FR)

( * ) Notice: Subject to any disclaimer, the term of this patent is extended or adjusted under 35 U.S.C. 154(b) by 260 days.

(21) Appl. No.: 17/908,846

(22) PCT Filed: Mar. 2, 2021

(86) PCT No.: PCT/EP2021/055140
§ 371 (c)(1),
(2) Date: Sep. 1, 2022

(87) PCT Pub. No.: WO2021/175828
PCT Pub. Date: Sep. 10, 2021

(65) Prior Publication Data
US 2023/0149743 A1 May 18, 2023

(30) Foreign Application Priority Data
Mar. 2, 2020 (FR) ..................................... 2002062

(51) Int. Cl.
*A61N 7/00* (2006.01)
(52) U.S. Cl.
CPC ........ *A61N 7/00* (2013.01); *A61N 2007/0043* (2013.01); *A61N 2007/0052* (2013.01)

(58) Field of Classification Search
CPC .............. A61N 7/00; A61N 2007/0052; A61N 2007/0043; A61M 1/3626; A61M 2205/3375
See application file for complete search history.

(56) References Cited

U.S. PATENT DOCUMENTS

| 4,791,915 | A | 12/1988 | Barsotti et al. |
| 2003/0028341 | A1 | 2/2003 | Fallon et al. |
| 2004/0002652 | A1 | 1/2004 | Phelps et al. |
| 2012/0083717 | A1 | 4/2012 | Alleman et al. |
| 2014/0171802 | A1 | 6/2014 | Kuroiwa et al. |
| 2015/0157299 | A1 | 6/2015 | Hopple et al. |

(Continued)

FOREIGN PATENT DOCUMENTS

| EP | 0050040 A2 | 4/1982 |
| EP | 1626779 A2 | 2/2006 |
| EP | 2324769 A1 | 5/2011 |

(Continued)

*Primary Examiner* — Gerald Johnson
(74) *Attorney, Agent, or Firm* — BCF LLP

(57) ABSTRACT

The present invention relates to an apparatus for treating a pathology, comprising:
 an ultrasonic generation device (1),
 a remote control unit (2) to supply electricity to the device (1),
 electrical connection means (31, 32) between the device (1) and the control unit (2),
remarkable in that the control unit (2) is programmed to assess the quality of the acoustic coupling between the ultrasonic device (1) and a tissue to be treated.

19 Claims, 7 Drawing Sheets

(56) References Cited

U.S. PATENT DOCUMENTS

2019/0209228 A1   7/2019  Canney
2021/0204915 A1*  7/2021  Vortman ................ A61B 8/54

FOREIGN PATENT DOCUMENTS

| EP | 2539021 | B1 | 2/2016 |
| EP | 3216410 | A1 | 9/2017 |
| FR | 3053597 | A1 | 1/2018 |
| JP | H09297160 | A | 11/1997 |
| WO | 2018007500 | A1 | 1/2018 |
| WO | 2018185767 | A1 | 10/2018 |
| WO | 2020013868 | A1 | 1/2020 |

* cited by examiner

METHOD AND SYSTEM FOR DETECTING A FAULT IN ACOUSTIC COUPLING BETWEEN AN ULTRASONIC DEVICE AND A TISSUE TO BE TREATED

CROSS-REFERENCE TO RELATED APPLICATIONS

This application is a national phase filing under 35 U.S.C. § 371 of International Application No. PCT/EP2021/055140 filed on Mar. 2, 2021, which claims benefit of priority from French Patent Application No. 2002062 filed Mar. 2, 2020, the contents of each of which are hereby incorporated by reference in their entirety.

FIELD OF THE INVENTION

The present invention relates to the general technical field of ultrasonic devices—for example intracorporeal or implantable devices—intended to be electrically connected to a remote control unit.

Such devices can in particular be implanted in humans and mammals to help a practitioner in establishing a diagnosis and/or treating a pathology.

BACKGROUND OF THE INVENTION

An apparatus for treating brain disorders is known from document WO 2018/007500. Referring to FIG. 1, such an apparatus is composed of:
  an ultrasonic device 1 made of non-ferromagnetic material,
  a control unit 2 remote from the ultrasonic device 1, and
  connection means for the connection between the ultrasonic device 1 and the control unit 2.

The ultrasonic device 1 is intended to be positioned in a burr hole made in a patient's skull. It is advantageously compatible with the Magnetic Resonance Imaging (MRI) technique, and comprises:
  at least one transducer 12 for the generation of ultrasonic waves for treating a brain disease,
  fixing means 13 for fixing the transducer 12 in the patient's skull,
  one (or more) electrical connection terminal(s) 14 intended to cooperate with the connection means.

The control unit 2 is intended to supply electrical energy to the ultrasonic device 1, and to adjust its operating parameters.

The connection means are intended to electrically link the ultrasonic device 1 to the control unit 2. They generally comprise:
  one (or more) electrical connection cable(s) 31, one end of which is linked to the control unit, and
  one (or more) transdermal needle(s) 32 connected to the other end of the cable 31.

The operating principle of this apparatus is as follows. Once the ultrasonic device 1 is implanted in the skull of the patient, a succession of treatment sessions are provided to the latter in order to treat the pathology affecting him. At each new treatment session, the ultrasonic device 1 is linked to the control unit 2 via the connection means.

The practitioner links the cable 31 to the control unit 2 then inserts the needle 32 through the patient's skin up to the terminal 14 of the ultrasonic device.

Once the end of needle 32 is connected to terminal 14, the control unit 2 can be activated to supply the ultrasonic device 1 with electrical energy.

The detection method described in WO 2018/007500 proposes, prior to the implementation of the treatment, to check the quality of the electrical connection between the ultrasonic device 1 and the control unit 2.

More specifically, the system and the method described in WO 2018/007500 allow detecting different types of defective electrical connection such as:
  the absence of electrical connection between the cable 31 and the control unit 2,
  the absence of electrical connection between the transdermal needle and the terminal 14.

Checking the quality of the electrical connection between the ultrasonic device 1 and the control unit 2 prior to the implementation of the treatment allows limiting the risks of ineffectiveness in the treatment.

However, other parameters can influence the effectiveness of the treatment, and in particular the quality of the acoustic coupling between the ultrasonic device 1 and the tissue to be treated.

One aim of the present invention is to propose a method and a system allowing the practitioner to detect a possible fault in the quality of the acoustic coupling between:
  an ultrasonic device, and
  a tissue to be treated.

The ultrasonic device may also undergo degradation over time. In particular, the operation of one (or more) transducer(s) of the device may fail, for example if an electrical connection of one (or more) transducer(s) is altered (short circuit or open circuit), for example upon disengagement of one (or more) connection tab(s) from one (or more) transducer(s).

Another aim of the invention is to propose a method and a system allowing the practitioner to detect an operating fault of one (or more) transducer(s) of the ultrasonic device.

BRIEF DESCRIPTION OF THE INVENTION

To this end, the invention proposes an apparatus for treating a pathology, comprising:
  an ultrasonic device including at least one transducer able to generate ultrasonic waves, the transducer having a front face intended to be positioned facing a target medium,
  a remote control unit for determining and monitoring operating parameters of the ultrasonic device, and supplying it with electricity for at least one treatment cycle, each treatment cycle being preceded by a wait cycle,
  electrical connection means between the ultrasonic device and the control unit,
remarkable in that the control unit is programmed to implement an estimation phase of the quality of an acoustic coupling between the ultrasonic device and the target medium, said estimation phase comprising:
  the emission, by the control unit, of at least one monitoring signal, each monitoring signal having a respective frequency,
  the measurement, by the control unit, of at least one reflected signal, each reflected signal corresponding to a respective monitoring signal,
  the processing of the reflected signal to detect:
    either the presence of a liquid in the ultrasonic device,
    or the presence of a reflective material, such as a gas bubble, between said and at least one transducer and the target medium.

Preferred but non-limiting aspects of the present invention are as follows:
- the estimation phase can comprise a step of detecting the presence of liquid in the ultrasonic device, said step including the following sub-steps:
  - the emission, by the control unit, of a leakage current monitoring signal at a leakage current monitoring frequency,
  - the measurement, by the control unit, of a reflected leakage current monitoring signal corresponding to the portion of the leakage current monitoring signal that has not been absorbed by the ultrasonic device,
  - the processing of the reflected leakage current monitoring signal to detect the presence of a liquid in the ultrasonic device;
- the leakage current monitoring frequency can be a frequency that does not belong to an operating frequency range of the transducer, in particular a frequency on the order of 600 kHz for a transducer whose working frequency is equal to 1 MHz;
- the estimation phase can comprise a step of detecting the presence of a gas bubble, said step including the following sub-steps:
  - the emission, by the control unit, of a gas monitoring signal at a gas monitoring frequency,
  - the measurement, by the control unit, of a reflected gas monitoring signal corresponding to the portion of the gas monitoring signal that has not been absorbed by the ultrasonic device,
  - the processing of the reflected gas monitoring signal to detect the presence of a gas bubble between the transducer and the target medium.
- the gas bubble monitoring frequency can be a frequency that belongs to an operating frequency range of the transducer, more specifically a frequency greater than 90% of a working frequency of the transducer, in particular a frequency on the order of 962 kHz for a transducer whose working frequency is equal to 1 MHz;
- the step of detecting the presence of a gas bubble can be implemented for each transducer for at least one wait cycle, said step further including a step consisting in:
  - activating each transducer for which no gas bubble has been detected, the activated transducers being able to be supplied with electrical energy for the generation of ultrasonic treatment waves during at least one treatment cycle subsequent to said and at least one wait cycle,
  - deactivating each transducer for which a gas bubble has been detected, the deactivated transducers not being supplied with electrical energy during the treatment cycle subsequent to said and at least one wait cycle.
- each treatment session can comprise a plurality of treatment cycles during which the device emits ultrasonic treatment waves towards a tissue to be treated, each treatment cycle being preceded by a wait cycle, the control unit being programmed to implement:
  - the step of detecting the presence of a gas bubble during each wait cycle,
  - the step of detecting the presence of a liquid during each treatment cycle;
- the steps of detecting the presence of liquid and gas can be implemented sequentially, the step of detecting the presence of liquid being implemented subsequently to the step of detecting the presence of a gas bubble;
- the ultrasonic device can include a casing in which each transducer is housed, the casing including a bottom facing the front face of each transducer, the bottom being made of Poly-Ether-Ether-Ketone, the thickness of the bottom being comprised, for a working frequency of the transducer equal to 1 MHz, between 0.3 mm and 0.8 mm, preferably comprised between 0.3 mm and 0.6 mm, and even more preferably substantially equal to 0.4 mm±0.05 mm.

The estimation phase can comprise a step of detecting the operation of each transducer, particularly of detecting a short circuit or an open circuit. For this, the control unit sends to each transducer a voltage at frequency $F_0$, this frequency being advantageously zero (DC voltage).

The invention also proposes an implantable ultrasonic device including at least one transducer able to generate ultrasonic waves, the transducer including:
- at least one electroacoustic element made of a piezoelectric material, and
- a casing including a bottom, at least one side wall and one upper wall, the casing forming a sealed housing intended to contain said and at least one electroacoustic element, remarkable in that the material constituting the bottom of the casing is Poly-Ether-Ether-Ketone (PEEK).

Preferred but non-limiting aspects of the present invention are as follows:
- the electroacoustic element includes a front face intended to be positioned facing the tissue to be treated and a rear face opposite to the front face, the transducer comprising a layer reflecting the acoustic waves, such as a layer of air, said layer extending over the rear face of the electroacoustic element;
- it will be understood hereinafter that when a layer A is mentioned as being "extending over" a layer B, the latter can be directly on the layer B, or can be located above the layer B and separated from said layer B by one or more intermediate layers playing a negligible acoustic role at the working frequency of the transducer;
- the front face of the electroacoustic element is in contact with the bottom of the casing;
- it will be understood below that when a layer A is mentioned as being "in contact with" a layer B, the latter can be directly in contact with the layer B, or can be separated from said layer B by one or more intermediate layer(s) playing a negligible acoustic role at the working frequency of the transducer;
- the material constituting said and at least one side wall and the cover of the casing is also Poly-Ether-Ether-Ketone (PEEK);
- the thickness of the bottom of the casing satisfies the following relation:

$$E_{Bottom}=(V_{sound}/4F_{Working})\times(0.8\pm0.4),$$

Where:
- $E_{Bottom}$ corresponds to the thickness of the bottom of the casing (in mm),
- $V_{sound}$ corresponds to the speed of sound in the material constituting the bottom of the casing, and
- $F_{Working}$ corresponds to the working frequency of the transducer 12 (in MHz), said working frequency being chosen in the useful frequency band of the transducer 12.
- for a working frequency on the order of 1 MHz, the thickness of the PEEK bottom is chosen between 0.3 mm and 0.8 mm, preferably between 0.3 mm and 0.6 mm, and even more preferably substantially equal to 0.4 mm (±0.05 mm).

The invention proposes an apparatus for treating a pathology comprising:
- an ultrasonic device including an electronic card and at least one transducer electrically connected to the electronic card, the transducer being able to generate ultrasonic waves,
- a remote control unit for determining and monitoring operating parameters of the ultrasonic device, and supplying it with electricity during at least one treatment cycle, each treatment cycle being preceded by a wait cycle,
- electrical connection means between the ultrasonic device and the control unit, remarkable in that the control unit is programmed to implement a detection phase of an operating fault of each transducer of the ultrasonic device, said detection phase comprising:
- the emission, by the control unit, of at least one test signal, each monitoring signal having a zero frequency,
- the measurement, by the control unit, of at least one reflected test signal,
- the processing of the reflected test signal to detect:
  - either a short circuit in the ultrasonic device,
  - or an electrical connection fault between said and at least one transducer and the electronic card.

BRIEF DESCRIPTION OF THE DRAWINGS

Other advantages and characteristics of the method and of the system according to the invention will emerge better from the following description of several variants of embodiments, given by way of non-limiting examples, from the appended drawings in which.

DETAILED DESCRIPTION OF THE INVENTION

Figure 1:
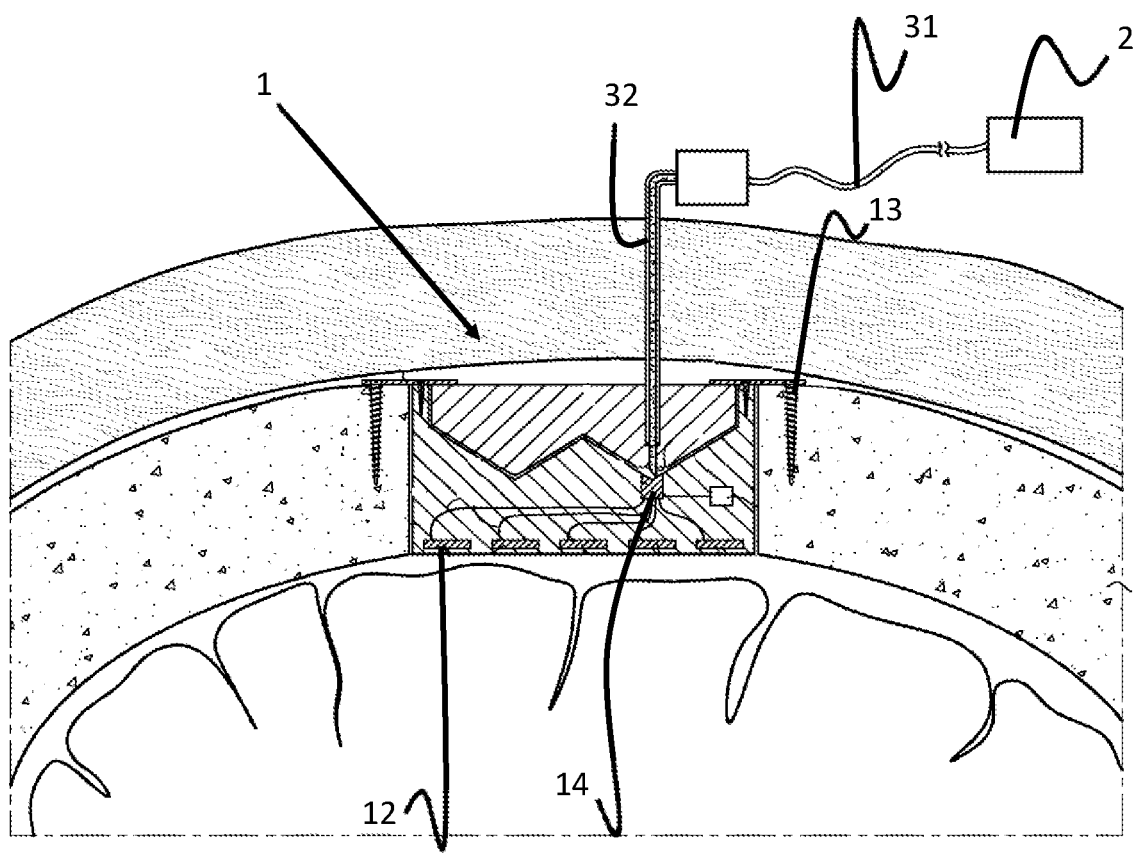
FIG. 1 schematically illustrates one example of an apparatus for treating a brain condition, including an ultrasonic device electrically connected to a remote control unit with connection means (transdermal needle+cable)

Different examples of the system and method for estimating the quality of an acoustic coupling will now be described with reference to the figures. In these different figures, the equivalent elements are designated by the same reference numeral.

This estimation system and method allow a practitioner to check whether the acoustic coupling between an ultrasonic device implanted in the body of a patient and a tissue to be treated is correctly achieved.

In the following, the estimation system and method will be described with reference to the apparatus presented in document EP 2 539 021 to which the international application WO 2018/007500 refers.

However, it is obvious to those skilled in the art that the system and the method according to the invention can be implemented with any type of treatment apparatus including an implantable or non-implantable device to be acoustically coupled to a tissue to be treated.

1. Generalities 1.1. Treatment Apparatus

As previously described, the apparatus comprises:
- an ultrasonic device 1,
- a control unit 2, and
- connection means.

The ultrasonic device 1 is intended to be implanted in a skull bone of a patient. It includes:
- an electronic card suitable for exchanging power supply and monitoring electrical signals with the remote control unit,
- a transducer 12 connected to the electronic card for the generation of ultrasonic waves, and
- a connection terminal 14 intended to receive a transdermal needle 32 of the electrical connection means.

In the following, it will be considered that the ultrasonic device 1 has been implanted, that is to say:
- the ultrasonic device 1 has been inserted into a cranial opening so that the transducer(s) extend(s) facing a tissue to be treated,
- the ultrasonic device 1 has been fixed to the periphery of the cranial opening by any means known to those skilled in the art (anchoring screw, bonding, etc.), then
- the patient's scalp and head muscles have been repositioned to cover the ultrasonic device 1.

The remote control unit 2 allows supplying electrical energy to the ultrasonic device 1, adjusting its operating parameters and receiving a signal reflected by the device. Since such a control unit 2 is known to those skilled in the art, it will not be described in more detail below.

The connection means allow electrically connecting the ultrasonic device 1 and the control unit 2. The connection means include in particular:
- the transdermal needle 32 able to be plugged onto the connection terminal of the ultrasonic device,
- an electrically conductive cable 31, and
- a link socket (not represented) able to be plugged into a complementary socket of the control unit 2.

1.2. Principle of Using the Apparatus

Such an apparatus allows the treatment of a brain disease by implementing several treatment sessions prescribed by the practitioner.

At each new treatment session, the practitioner electrically connects the ultrasonic device 1 to the remote control unit 2 by using the connection means.

More specifically, the practitioner connects the link socket to the remote control unit 2.

The practitioner then inserts the transdermal needle 32 into the patient's scalp, and introduces the end of the needle 32 into a blind hole of the connection terminal 14 so as to finalize the electrical connection of the ultrasonic device 1 to the remote control unit 2.

Once the ultrasonic device 1 is connected to the control unit 2, a succession of treatment cycles are executed, each treatment cycle being preceded by a wait cycle.

During a wait cycle, the ultrasonic device 1 is deactivated during a wait period (on the order of 1 second). This deactivation is performed by not supplying the ultrasonic device 1 with electrical energy.

When the wait period expires, a treatment cycle is implemented. During the treatment cycle, the ultrasonic device 1 is supplied with electrical energy by the application, at the connection terminal, of an electrical excitation signal during a treatment period (on the order of 25 milliseconds).

This electrical excitation signal is emitted by the control unit 2 at a working frequency of the transducer(s) 12.

Within the context of the present invention, it is meant by "working frequency" (or "treatment frequency") the emission frequency of the ultrasonic treatment waves emitted by the transducer(s) 12, this frequency also corresponding to the frequency of the electrical excitation signal making it possible to supply the ultrasonic device with electrical energy.

This working frequency is contained in a useful frequency band of the transducer 12 (i.e. operating frequency range of the transducer), the transducer 12 not operating (i.e. not generating ultrasonic waves) when an electrical signal of a frequency non-contained in this useful band is applied to it.

Advantageously, the transducers 12 can be chosen to have maximum efficiency at the working frequency. Thus, the working frequency corresponds to a treatment frequency of the ultrasonic waves used to treat the tissue to be treated.

In response to the application of the electrical excitation signal during the treatment period, the transducer 12 generates ultrasonic waves in the direction of the tissue to be treated.

When the treatment period has expired, a new wait cycle is implemented, and so on until the end of the session.

2. Transducer

Figure 2:
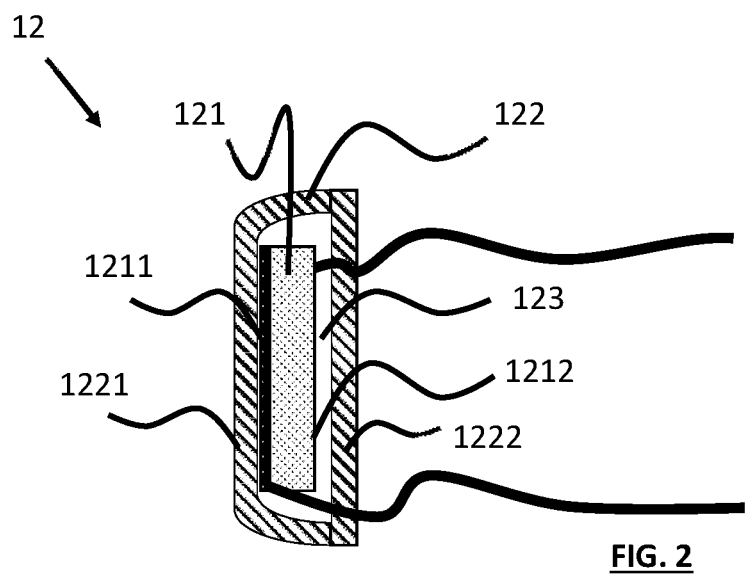
FIG. 2 is a schematic sectional representation of one of the transducers of the ultrasonic device.

Referring to FIG. 2, a partial sectional view of one of the transducers 12 of the ultrasonic device 1 is illustrated.

The transducer 12 includes:
one (or more) electroacoustic element(s) 121 intended for the therapy (the pulse trains are long and at a fixed frequency), and
a casing 122 containing the electroacoustic element.

2.1. Electroacoustic Element(s)

Each electroacoustic therapy element 121 is made of a piezoelectric material, such as "composite" (association of at least one piezoelectric material with one or more non-piezoelectric material(s) such as a polymer, etc.).

When the piezoelectric element 121 is of the "composite" type, its acoustic impedance is close to that of the tissue and a quarter-wave plate is not necessary, particularly when the device is intended for therapy.

Each electroacoustic element 121 is fixed on a bottom 1221 of the casing 122, for example by bonding by using a thin adhesive layer (which plays a negligible acoustic role at the working frequency of the transducer).

As illustrated in FIG. 2, the transducer 12 also comprises on the rear face 1212 of the electroacoustic element 121 a reflective layer (or backing), such as one (or more) layer(s) of air 123, the (or each) layer of air 123 extending over the rear face 1212 of the electroacoustic element 121.

Thus, the transducer 12 is devoid of absorbent material on the rear face 1212 of the electroacoustic element 121, unlike the acoustic imaging devices (using the technique called "pulse-echo" technique) in which the rear face of each electroacoustic element is covered with an absorbent material to prevent the element from resonating for a long time subsequently to its excitation.

Finally, a therapy transducer emits high energies (in particular due to the duration of the emissions) and must therefore not rise in temperature, especially if it is implanted in a patient.

The presence of absorbent material is therefore not desirable on the rear face of the electroacoustic element(s) 121 of the transducer(s) 12.

The reader will also appreciate that the layer of air disposed on the rear face of the electroacoustic element(s) 121 allows improving the energy efficiency of the transducer by reflecting all the acoustic energy generated by the element towards its front face.

Indeed, the piezoelectric element 121 comprises:
a front face 1211 directed towards the tissue to be treated, and
a rear face 1212 opposite to the front face 1211.

When the element 121 is supplied with electrical energy, it converts the electrical energy into mechanical energy and its vibration generates an acoustic wave which can propagate forwardly and backwardly of the element.

A layer of air 123 on the rear face 1212 of the piezoelectric element acts as a mirror and reflects the wave directed rearwardly of the element 121 in the direction of its front face 1211. Thus, the loss of part of the mechanical energy generated by the element 121 is avoided.

2.2. Casing

The casing 122 comprises the bottom 1221, a side wall and a cover 1222.

Advantageously, the material constituting the casing 122 can be Poly-Ether-Ether-Ketone (hereinafter referred to as "PEEK"). PEEK is particularly suitable for the manufacture of an implantable device due to its many qualities. PEEK is indeed a material which is:
highly sealed,
biocompatible,
electrically insulating, and
stable over time (when immersed).

In the embodiment illustrated in FIG. 2, for a working frequency on the order of 1 MHz, the thickness of the bottom 1221 of PEEK (facing the front face of the (or each) element 121) is chosen between 0.3 mm and 0.8 mm, preferably between 0.3 mm and 0.6 mm, and even more preferably substantially equal to 0.4 mm (±0.05 mm).

Of course, the choice of the thickness of the bottom is a function of the working frequency used for the transducer 12. Thus, the choice of the thickness as a function of the working frequency satisfies the following relation:

$$E_{Bottom} = (V_{sound}/4F_{Working}) \times (0.8 \pm 0.4),$$

Where:
$E_{Bottom}$ corresponds to the thickness of the bottom of the casing (in mm),
$V_{sound}$ corresponds to the speed of sound in the material constituting the bottom of the casing, and
$F_{Working}$ corresponds to the working frequency of the transducer 12 (in MHz), said working frequency being chosen in the useful frequency band of the transducer 12.

Such a choice of thickness for the bottom 1221 of the casing 122 is contrary to the general knowledge of those skilled in the art who would choose the thinnest possible bottom thickness in order to:
limit the absorption, by the bottom of the casing 122, of the ultrasonic energy emitted by the element(s) 121, and
reduce the volume of the implantable ultrasonic device.

On the contrary, this choice of bottom thickness 1221 (in the case of a PEEK bottom) is made to facilitate the detection of poor acoustic coupling between the ultrasonic device 1 and the tissue to be treated.

Indeed, the use of a PEEK bottom 1221 with a thickness substantially equal to 0.4 mm (±0.05 mm) allows facilitating the detection of a gas bubble between the transducer 12 and the tissue to be treated, the electrical absorption spectra being very different depending on whether the bottom is in acoustic contact with a gas on the one hand, or with the propagation medium (in this case: the dura mater) on the other hand.

A transducer 12 can include several piezoelectric elements 121 mounted in the same casing 122. Each casing is sealed.

Figure 3A:
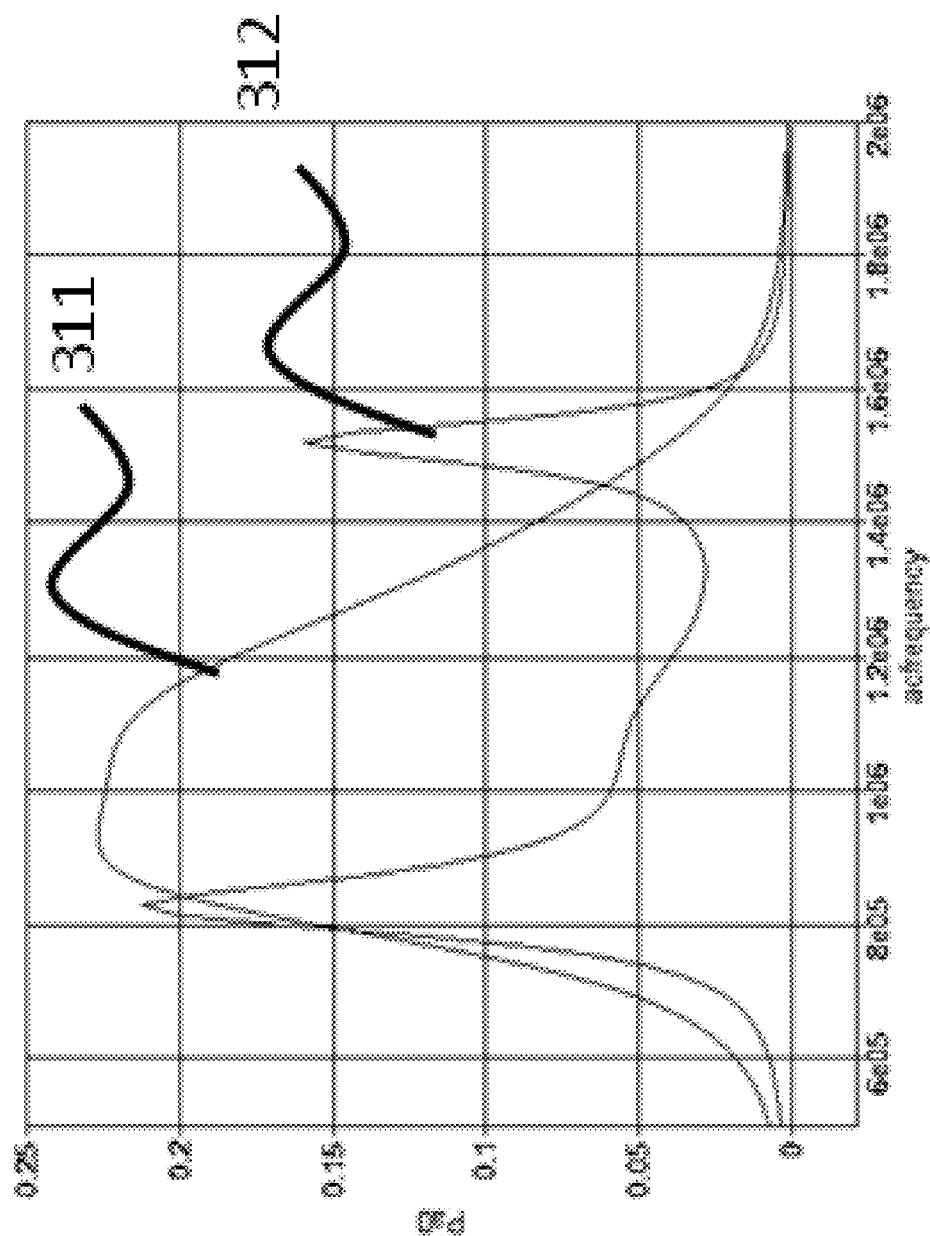
FIGS. 3A, 3B, and 3C illustrate the absorption spectra of the electrical power of the therapy transducers.
Figure 3B:
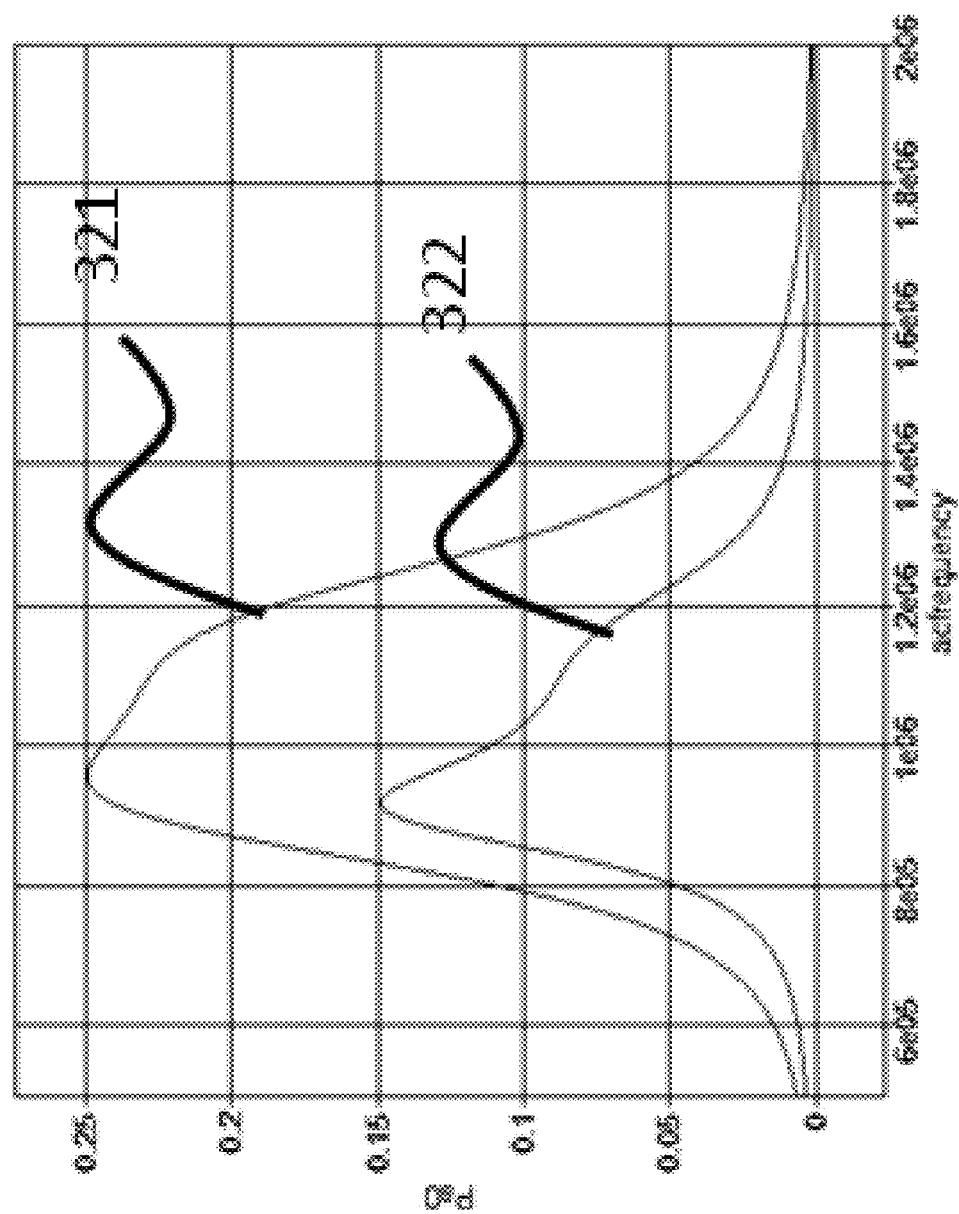
Figure 3C:
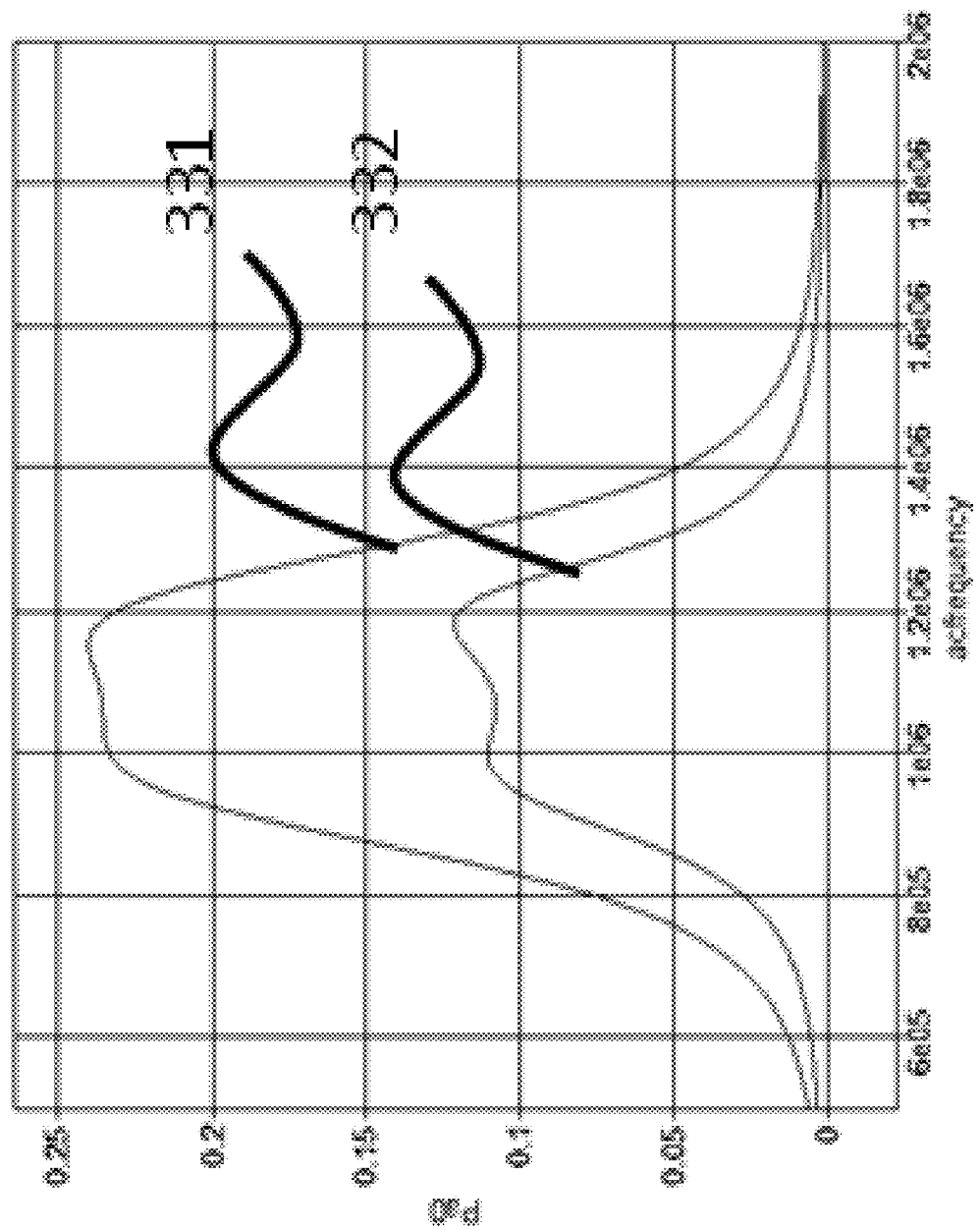

As an indication, FIGS. 3A, 3B, and 3C illustrate absorption spectra in electrical power (active power) of transducers associated with bottom casings 1221 of different thicknesses. The ordinate $P_{a0}$ of the graphs corresponds to the power absorbed by the transducer for an incident power of 250 mW. Note that an electrical impedance matching has been inserted between the transducer and the generator:

the first absorption spectrum (referenced 311 in the case of an acoustic coupling with the propagation medium, and referenced 312 in the case of an acoustic coupling with a gas) corresponds to a transducer associated with a PEEK bottom of thickness equal to 0.4 mm, the second absorption spectrum (referenced 321 in the case of an acoustic coupling with the propagation medium, and referenced 322 in the case of an acoustic coupling with a gas) corresponds to a transducer associated with a PEEK bottom of thickness equal to 0.2 mm, the third absorption spectrum (referenced 331 in the case of an acoustic coupling with the propagation medium, and referenced 332 in the case of an acoustic coupling with a gas) corresponds to a transducer associated with a PEEK bottom of zero thickness that is to say a casing devoid of bottom (the front face of the transducer being only covered with a layer of parylene).

As it clearly emerges from these FIGS. 3A, 3B and 3C, with a PEEK thickness of 400 μm, it is possible to take advantage of emissions at different frequencies to check the acoustic coupling between the transducer 12 and the tissue to be treated.

Thus, for a working frequency on the order of 1 MHz, the choice of a PEEK casing 122 whose bottom has a thickness comprised between 0.3 mm and 0.8 mm, preferably comprised between 0.3 mm and 0.6 mm, and even more preferably substantially equal to 0.4 mm (±0.05 mm) allows:

increasing the bandwidth for the therapy (being able to use a wider frequency range, being more robust to variability), without reducing the electroacoustic efficiency, increasing the electrical insulation, the biocompatibility and the longevity of the ultrasonic device; indeed, it is known that PZT ((Lead zirconate titanate) ceramics are not biocompatible (presence of lead), that parylene (which can be used as a protective film to cover each transducer) is porous, and that PZT or "composite" type materials drift with humidity over time.

More generally, it is possible to compare the reflected power spectra (or electrical impedance measurements) with a reference model or template (composed of a minimum reference value curve and of a maximum reference value curve). If the curve representative of the measured reflected power spectra is not contained in the template, this is representative of a fault. By looking at what frequency the reflected power spectrum is outside the template, it is possible to define this fault (air, connection, short circuit, faulty transducer, etc.).

It is meant by "incident power" the power transmitted to the transducer 12 by the control unit 2. It is meant by "active power" the power consumed by the transducer 12 (incident power—reflected power: part is converted into heat and the other in ultrasound). It is meant by "reflected power" the power flowing from the transducer 12 to the control unit 2.

Similarly, the reflected electrical signal ($\phi r$) and the incident electrical signal ($\phi_0$) are defined as the amplitudes of the reflected and incident electrical waves.

The reader will appreciate that it is possible to acquire the active power/reflected power/impedance spectra according to several methods, for example:

Continuously (for example over the range 0.2-1.6 MHz) by emitting a chirp type frequency-modulated test signal, or a very short signal and carrying out a Fourier analysis, Or discreetly, (which allows limiting the cost of the associated electronics) by emitting several test pulses at different frequencies judiciously chosen to allow detecting several types of faults from a limited number of pulses of different frequencies (for example four pulses at four different frequencies).

2.3. Advantages Associated with the Configuration Described Above

The configuration of the transducer described above (reflecting layer on the rear face of the piezoelectric element and PEEK layer on the front face of the piezoelectric element) allows increasing the ability to discriminate between the presence of air and the presence of water at the front face of the transducer that is to say the verification of the correct coupling when the transducer is implanted. As the transducer (air+piezo-composite+¼ wave) is very well adapted to water and is not damped at its rear face, the ultrasonic waves can only be damped by the front face (water/brain coupling). Thus, the presence or absence of water on the front face has a very great influence on the electrical impedance of the transducer.

The configuration of the transducer also allows:

improving the bandwidth of the transducer without reducing the electroacoustic efficiency, which allows more flexibility of use;

increasing the electrical insulation, the biocompatibility and the longevity of the transducer.

3. Issue Associated with the Use of the Treatment Apparatus

As indicated previously, the quality of the acoustic coupling (between the ultrasonic device and the medium containing the tissue to be treated) can vary over time.

For example, during a session, a gas bubble may be formed between the (or one of the) transducer(s) 12 and the tissue to be treated. Similarly, a gas bubble may be trapped between the transducer and the tissue to be treated during the operation of implanting the device. Also, bone calcification can be formed over time between the transducer and the tissue to be treated. The presence of such a reflective material (gas bubble or bone growth) between the transducer and the tissue limits the propagation of the ultrasonic waves generated by the transducer 12 towards the tissue to be treated, which has the consequence of limiting the effectiveness of the treatment.

In addition, liquid can enter the device 1, for example during the insertion of the transdermal needle 32 into the connection terminal 14, this liquid possibly causing a short circuit (or more specifically the appearance of a leakage current) limiting the effectiveness of the treatment.

This is why it is desirable to estimate the quality of the acoustic coupling between the ultrasonic device 1 and the tissue to be treated in order to limit the risks of ineffectiveness in the treatment.

Furthermore, one (or more) of the transducers may have a fault such as a short circuit or an open circuit (for example following the disengagement of one (or more) connection tab(s) from one (or more) transducer(s).

This is why it is also desirable to detect an operating fault of one (or more) transducer(s) of the ultrasonic device in order to limit the risks of ineffectiveness in the treatment.

The reader will appreciate that these two test phases (i.e. estimation of the quality of the coupling and detection of an operating fault of a transducer) can be carried out independently of each other, or jointly. Thus in some embodiments, the treatment apparatus can be configured to:
  perform only one estimation of the quality of the acoustic coupling, or
  perform only one detection of an operating fault of one (or more) transducer(s) of the ultrasonic device, or
  perform both an estimation of the quality of the acoustic coupling and a detection of an operating fault of one (or more) transducer(s) of the ultrasonic device.

4. Method for Assessing the Quality of the Acoustic Coupling

Figure 4:
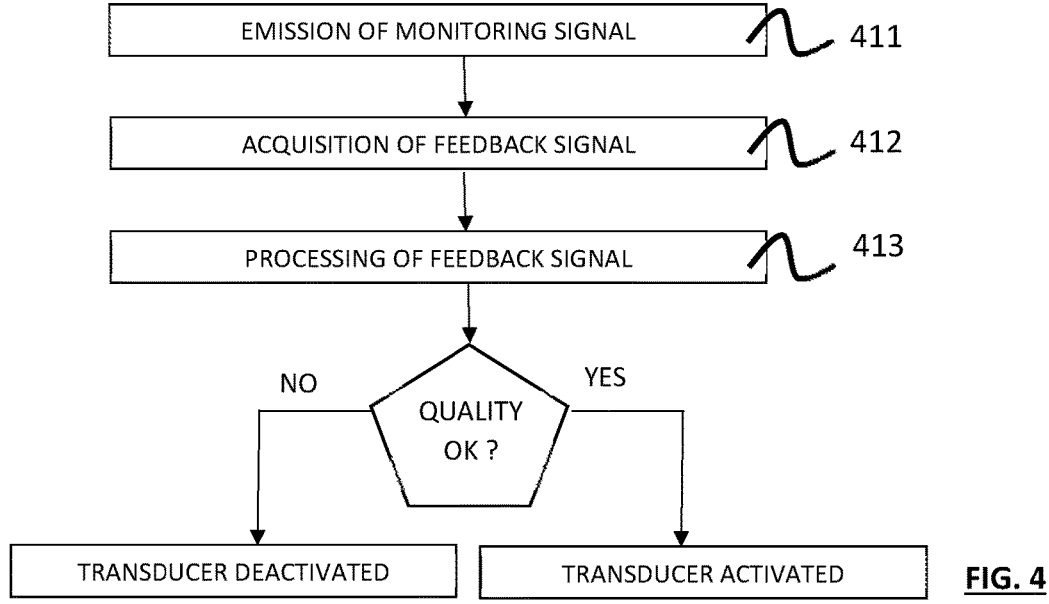
FIG. 4 is a schematic representation of the main steps of a method for estimating the quality of an acoustic coupling.

Referring to FIG. 4, the Method for Estimating the Quality of the Acoustic Coupling comprises the following steps:
  the emission 411, by the control unit 2, of at least one monitoring signal,
  the acquisition 412, by the control unit 2, of at least one feedback signal,
  the processing 413 of the feedback signal to obtain information on the quality of the acoustic coupling between the ultrasonic device 1 and the tissue to be treated, said processing allowing:
    the activation of each transducer 12 for which the quality of the acoustic coupling is above a quality threshold,
    the deactivation of each transducer 12 for which the quality of the acoustic coupling is below a quality threshold.

Following the assessment of the quality of the acoustic coupling, the activated transducers can (during each treatment cycle) be supplied with electrical energy so that they generate treatment ultrasonic waves towards the tissue to be treated. The deactivated transducers are for their part not supplied with electrical energy by the control device 2.

Each monitoring signal is emitted at a low electrical energy compared to the excitation signal (on the order of 1% of the energy required for the treatment). More specifically, the electrical power of each monitoring signal is such that any ultrasonic waves generated by the ultrasonic device (in response to the monitoring signal) do not cause any tissue effect.

In order to detect the possible presence of one of these factors (i.e. of fluid in the ultrasonic device and/or gas/bone bubble between the bottom of the casing and the propagation medium, and/or operating fault of the transducer), several monitoring signals are each emitted at one frequency. For each signal, the control unit 2 emits a signal of known amplitude and frequency to the device 1. This signal not being perfectly impedance-matched, in particular due to an imperfect acoustic matching between the transducer 12 and the tissue—part of the signal (feedback signal) is reflected back to the device. The control unit 2 measures the amplitude of this reflected signal and deduces a reflection rate therefrom. The control unit 2 can also measure the impedance of the circuit of the implanted ultrasonic device up to the transducer.

More specifically, the method comprises the following steps for each transducer 12 of the ultrasonic device 1:
  application of several monitoring signals at several frequencies, each monitoring signal having a respective frequency,
  measurement of a plurality of reflection rates of the monitoring signals, each measured reflection rate corresponding to a respective monitoring signal,
  comparison of the reflection rates with pre-established thresholds and estimation of the quality of the coupling between the considered transducer 12 and the tissue.

The reflection rate corresponds to the proportion of the monitoring signal reflected by the transducer 12. The reflection rate (B) of a monitoring signal can be defined as the ratio between the reflected electrical signal ($\phi r$) and the incident electrical signal ($\phi_0$):

$$B = \phi r / \phi_0.$$

In practice, the step of applying the monitoring signals consists in sequentially applying two, three or four monitoring signals each having a respective frequency.

The frequencies of the monitoring signals are chosen to maximize the discrimination (of problem detection sensitivity) for each of the following four factors:
  Electrical connection fault as proposed in WO 2018/007500,
  Presence of a gas bubble between the transducer 12 and the tissue to be treated,
  Presence of fluid in the ultrasonic device (for example at the connection terminal containing the end of the transdermal needle 32),
  Operating fault of a transducer (short circuit or open circuit)

The choice of the frequencies is made based on:
  the absorption spectra, and
  the standard deviations of the absorption spectra
in a population of the manufactured transducers.

In particular, the frequencies of the monitoring signals are chosen such that the following ratio is maximum:

$$(\text{Mean}_{water} - K\sigma_{water}) / (\text{Mean}_{air} + K\sigma_{air}),$$

With:
  "Mean", the mean of the absorption measurements on a sample population at a considered frequency,
  "$\sigma$", the standard deviation of the absorption measurements on the sample population at the considered frequency (the slight variability in the operation of the transducers due to the manufacturing tolerances explaining the presence of this standard deviation),
  "K" an integer comprised between 1 and 3.

The advantage of using different monitoring signals each having a respective frequency (associated with the choice of thickness of the casing bottom) is to make the assessment method very discriminating with respect to the different factors that may deteriorate the quality of the coupling. In other words, the method according to the invention allows defining whether an insufficient coupling quality is due to:
- a connection fault,
- the presence of a gas bubble, or
- the presence of fluid.
- an operating fault of one of the transducers.

It is thus possible to inform the practitioner more accurately about the nature of the problem detected so that he can implement the most suitable solution to solve the problem detected.

4.1. Frequencies

In order to determine possible coupling faults making the treatment impossible or ineffective, different monitoring signals at different frequencies are emitted, each monitoring signal having a frequency (preferably) different from the treatment frequency $F_1$.

4.1.1. Frequency of the Monitoring Signal for the Detection of a Short Circuit Particularly, the monitoring signal for the detection of a short circuit or a parasitic resistance (due to the presence of liquid at the connection terminal) is emitted at a frequency $F_2$.

This frequency $F_2$ is chosen much lower than the working frequency $F_1$ such that the power consumed by the transducer is low (less than 40% of the incident power).

More specifically, the frequency $F_2$ is chosen outside the useful frequency band of the transducer (i.e. operating frequency range of the transducer); thus a measured reflection rate (at the frequency $F_2$) much lower than 1 (i.e. non-zero power consumption) indicates the existence of a short circuit due to the presence of liquid in the ultrasonic device.

In particular, in one embodiment of the invention, the frequency $F_2$ of the monitoring signal used for the detection of a short circuit or a parasitic resistance is substantially equal to 0.6 MHz.

4.1.2. Frequency of the Monitoring Signal for the Detection of an Electrical Connection Fault The monitoring signal for the detection of an electrical connection fault (see WO2018007500) is emitted at a frequency $F_3$, different from the frequency $F_2$.

This frequency $F_3$ is chosen between the frequency $F_2$ and the working frequency $F_1$. In particular, in one embodiment of the invention, the frequency $F_3$ of the monitoring signal used for the detection of an electrical connection fault is substantially equal to 850 kHz.

Particularly, the frequency $F_3$ is chosen such that the power consumed by the transducer is independent of the medium located on the front face of the transducer. In other words, the frequency $F_3$ is chosen such that:
- the power consumed by the transducer is maximum (in particular greater than 40% of the incident power of the monitoring signal applied to the transducer) on the one hand, and such that
- the power consumed by the transducer when its front face is in contact with a gas is substantially equal to the power consumed by the transducer when its front face is in contact with a liquid or the tissue.

Thus, a measured reflection rate (at the frequency $F_3$) substantially equal to 1 (i.e. zero active (=consumed) power) indicates the absence of electrical connection between the ultrasonic device 1 (or one of the transducers 12 of the device 1) and the control unit 2.

4.1.3. Frequency of the Monitoring Signal for the Detection of a Gas Bubble The monitoring signal for the detection of a gas bubble between the transducer and the tissue to be treated is emitted at a frequency $F_4$ different from the frequencies $F_2$ and $F_3$.

Particularly, the frequency $F_4$ is chosen such that the power consumed by the transducer is:
- to a minimum when the front face of the transducer is facing a gas bubble (a transducer is considered in the air if the transmitted power is less than 64% of the incident power, and in water in the opposite case), and
- to a maximum when the front face of the transducer is facing a propagation medium such as the dura mater, the tissue or liquid.

This frequency $F_4$ is chosen higher than the frequency $F_3$ and slightly lower (i.e. between 1% and 10% lower, preferably 1% and 5% lower) or equal to the working frequency $F_1$.

In particular, in one embodiment of the invention, the frequency $F_4$ of the monitoring signal used for the detection of a gas bubble is substantially equal to 960 kHz (96% of the working frequency of the transducer).

Figure 5:
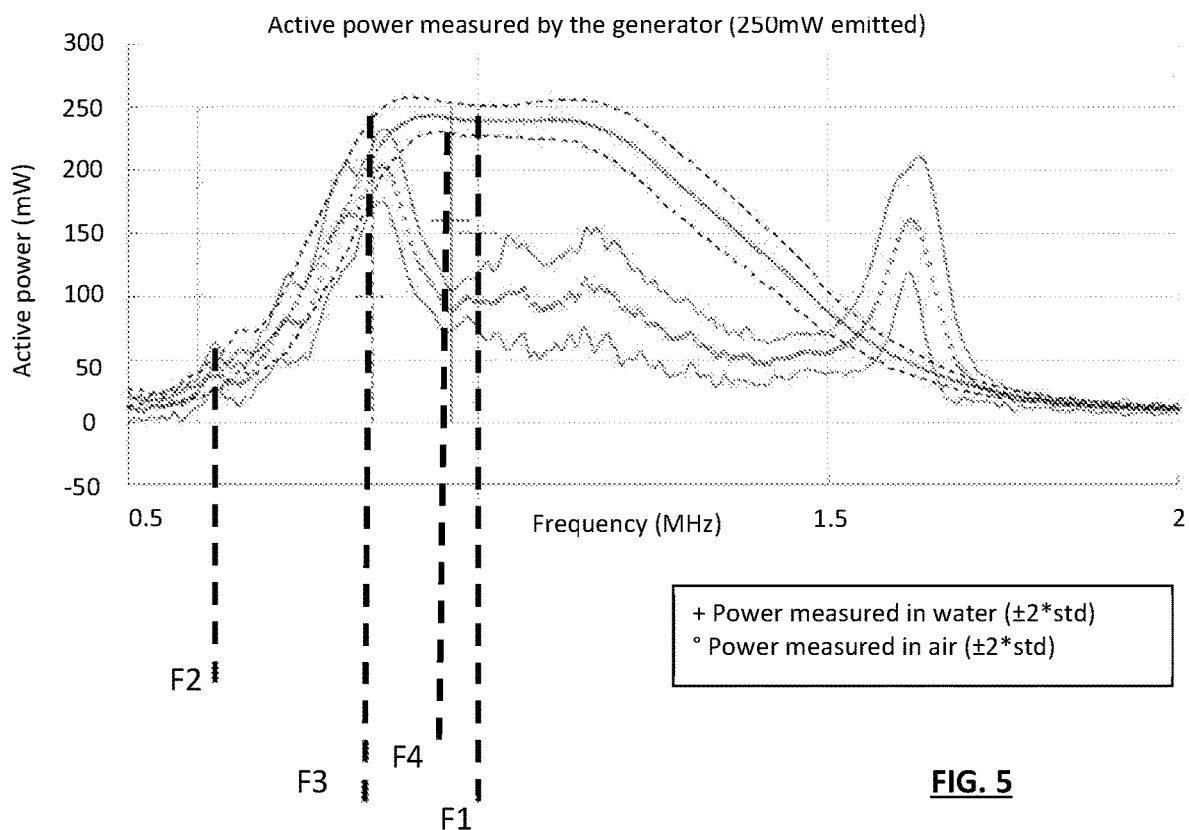
FIG. 5 is a curve illustrating, for a batch of transducers, the power consumed by each transducer as a function of the frequency of the applied electrical signal.

Thus, and as illustrated in FIG. 5 (which represents the power consumed by a batch of transducers as a function of the frequency of the applied electrical signal with a power of 250 mW), the frequencies used for the different monitoring signals are chosen so as to maximize the discrimination between the different types of faults that may influence the quality of the treatment.

4.1.4 Frequency of the Monitoring Signal for the Detection of an Operating Fault of a Transducer (DC Voltage: $F_0=0$)

The monitoring signal for the detection of an operating fault of a transducer is emitted at a zero frequency $F_0$ so that the monitoring signal has a DC voltage.

Thus, a DC voltage monitoring signal can be applied by the control unit to the implanted ultrasonic device. This monitoring signal at zero frequency $F_0$ allows detecting:
- either a dead short circuit in a transducer (zero impedance, when the transducer is activated),
- or a fault in a connection chamber (impedance too low if presence of liquid, in particular if the impedance is too low whether a transducer is controlled or not or regardless of the controlled transducer).

This test allows completing the test described in point 4.1.1. for the detection of a short circuit from a monitoring signal emitted at the frequency $F_2$.

4.2. Example of Implementation of the Estimation Method

Figure 6:
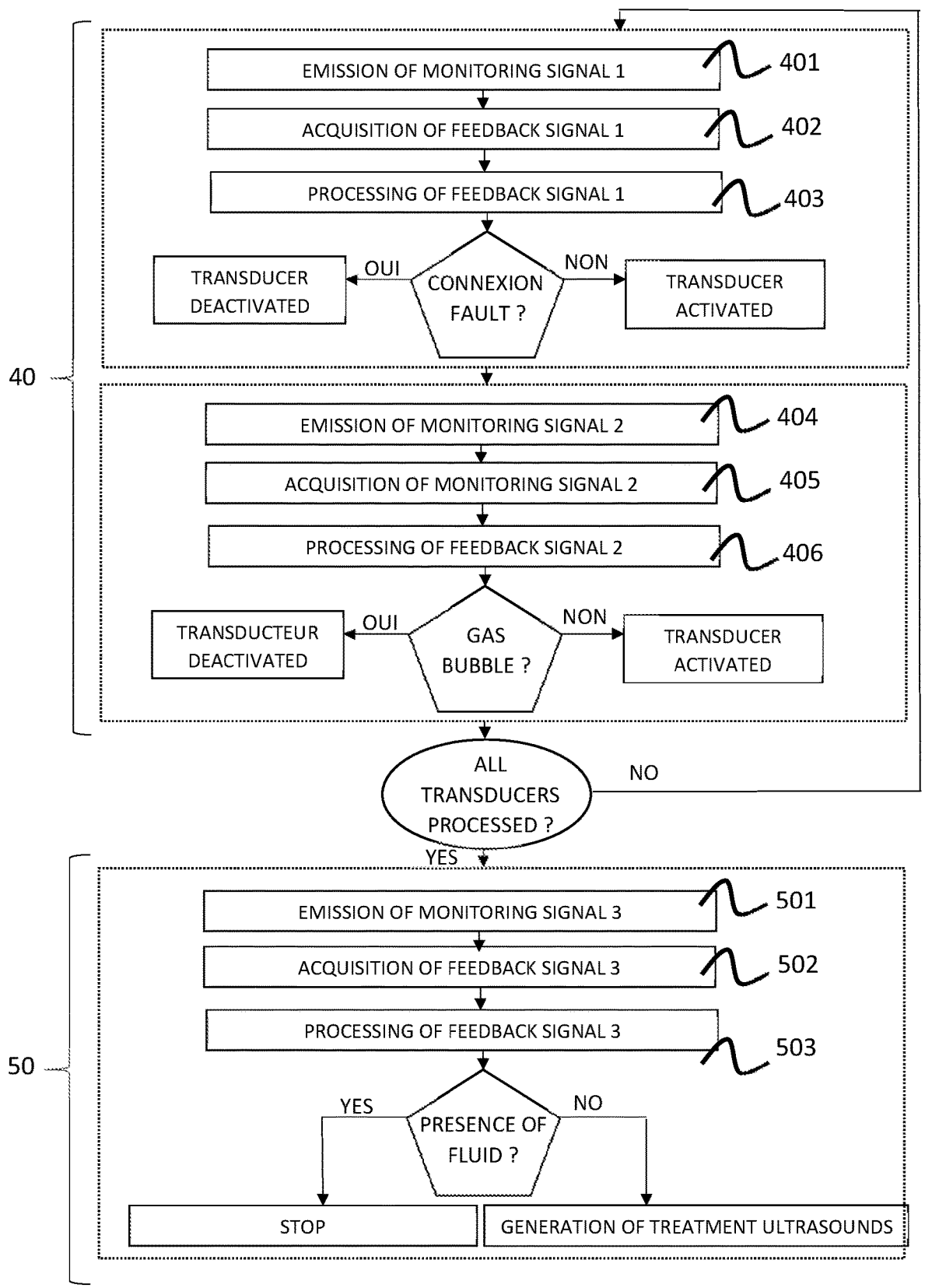
FIG. 6 is a schematic representation of one alternative embodiment of the method for estimating the quality of an acoustic coupling.

The operating principle of the estimation method will now be described in more detail with reference to FIG. 6. This estimation method allows detecting:
- the presence of air on the front face of the emitters,
- whether the emitters are functional,
- whether a fluid (such as water) is present inside the ultrasonic device.

In this embodiment, some detection steps of the method are carried out during each wait cycle, and others are carried out during each treatment cycle.

4.2.1. Wait Cycle

During each wait cycle, the method comprises:
- a first step of detecting an electrical connection fault, and
- a second step of detecting the presence of a gas bubble.

These first and second steps are implemented sequentially, for each transducer 12 of the ultrasonic device 1.

4.2.1.1. Electrical Connection Fault

The first step of detecting an electrical connection fault includes the sub-steps consisting in:
Emitting 401 a first monitoring signal at a first monitoring frequency $F_3$;

the first monitoring signal consists for example of a pulse signal with a power of 250 mW and a duration equal to 1 ms, the first frequency being chosen equal to 850 kHz, Acquiring 402 a first reflected monitoring signal corresponding to the portion of the first monitoring signal that has not been absorbed by the ultrasonic device:

the acquisition of the first reflected signal can consist in measuring the electrical power of the reflected signal (for example by using a directional coupler) or any other information representative of the power consumed by the transducer(s), Processing 403 the first reflected monitoring signal to detect a connection fault:

during the processing sub-step, information representative of the power consumed by the transducer is extracted from the first reflected signal, this information representative of the consumed power is compared with a first predefined threshold corresponding to 40% of the power of the first monitoring signal (namely 100 mW in the case of a first monitoring signal of 250 mW):

if the information representative of the consumed power is below the first threshold, then the transducer 12 is not correctly connected to the remote control unit 2 (i.e. detection of an absence of electrical link between the transducer and the control unit), if not, then the electrical connection between the considered transducer and the control unit is functional (i.e. no imperfection in the electrical connection between the transducer and the control unit).

4.2.1.2. Presence of Gas

The step of detecting the presence of a gas bubble includes the sub-steps consisting in:

Emitting 404 a second monitoring signal at a second monitoring frequency:

the second monitoring signal consists for example of a pulse signal with a power of 250 mW and a duration equal to 1 ms, the second frequency being chosen equal to 962 kHz, Acquiring 405 a second reflected monitoring signal:

here again, the acquisition of the second reflected signal can consist in measuring a "power absorbed" by the transducer, or a "reflection rate", or an electrical impedance, or any other information representative of a power consumed by the transducer, Processing 406 the second reflected monitoring signal to detect the presence of a liquid in the ultrasonic device:

information representative of the power consumed by the transducer (extracted from the second reflected signal) is compared with a second predefined threshold corresponding to 64% of the power of the second monitoring signal (namely 160 mW in the case of a second monitoring signal of 250 mW):

if the information representative of the consumed power is below the second threshold, then the medium extending facing the front face of the transducer is a gas (i.e. detection of a gas bubble between the transducer and the tissue to be treated), otherwise, the medium extending facing the front face of the transducer is a liquid or tissue (absence of gas bubble).

4.2.1.3. Detection of an Operating Fault of a Transducer

Figure 7:
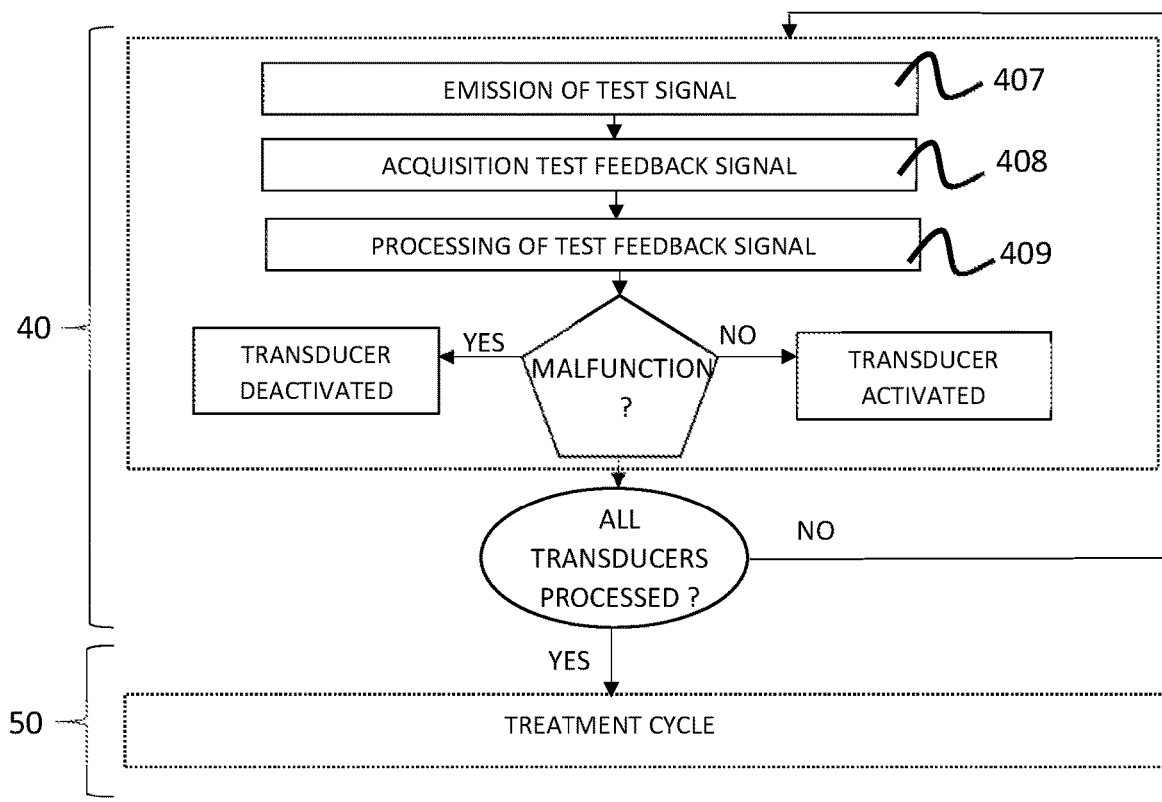
FIG. 7 is a schematic representation of one alternative embodiment of a method for detecting an operating fault of a transducer.

Referring to FIG. 7, the step of detecting an operating fault includes the sub-steps consisting in:

Emitting 407 a test signal at a zero monitoring frequency,

Acquiring 408 a reflected test signal, this acquisition of the reflected signal can consist in measuring a "power absorbed" by the transducer, or a "reflection rate", or an electrical impedance, or any other information representative of a power consumed by the transducer, Processing 409 the reflected test signal to detect an operating fault of a transducer: information representative of the power consumed by the transducer (extracted from the reflected test signal) is compared with first and second predefined test thresholds:

if the information representative of the consumed power is below the first test threshold (i.e. zero or too low impedance), then the transducer has a short circuit, if the information representative of the consumed power is above the second test threshold (i.e. too high or infinite impedance), then the connection between the transducer and the electronic card has an open circuit, otherwise, the transducer operates correctly (absence of operating fault).

This step of detecting an operating fault is carried out successively on each transducer of the ultrasonic device. The transducers for which an operating fault has been detected are deactivated while the transducers with no operating fault are activated.

4.2.2. Treatment Cycle

During each treatment cycle, the method comprises a third step of detecting the presence of a fluid in the ultrasonic device.

This detection step is implemented before each step of emitting treatment ultrasounds by the ultrasonic device. Thus, before each step consisting in supplying the transducer(s) with electrical energy to induce the generation of treatment ultrasounds, the step of detecting the presence of a fluid is implemented.

The third step of detecting the presence of a fluid comprises the sub-steps consisting in:

Emitting 501 a third monitoring signal at a third monitoring frequency $F_2$:

the third monitoring signal consists for example of a pulse signal with a power of 500 mW and a duration equal to 100 µs, the third frequency being chosen equal to 600 kHz, Measuring 502 a third reflected monitoring signal corresponding to the portion of the third monitoring signal that has not been absorbed by the ultrasonic device, Processing 503 the third reflected monitoring signal to detect the presence of a liquid in the ultrasonic device:

information representative of the consumed power is compared with a third predefined threshold corresponding to 40% of the power of the third monitoring signal (namely 200 mW in the case of a third monitoring signal of 500 mW):

if the information representative of the consumed power is below the third threshold, then the ultrasonic device does not contain any fluid (i.e. absence of short circuit), if not, then the ultrasonic device contains a fluid causing a short circuit.

Depending on the results of the different tests described above, the control unit 2 commands to the ultrasonic device 1 the emission of treatment ultrasonic waves.

Particularly, if no short circuit has been detected, the control unit 2 supplies the activated transducer(s) 12 of the ultrasonic device 1 for which no coupling fault has been detected (transducers electrically connected correctly, and whose front face does not extend facing a gas bubble). This supply step consists in applying to each activated transducer an electrical power supply signal with a power comprised between 7 and 8 Watts for a period of 24 ms.

As an indication, a table summarizing the different frequencies used for the implementation of the estimation phase of the coupling quality and the detection phase of an operating fault of a transducer is given below.

TABLE 1

Table of the frequencies and tests

| Frequency | Value | Denomination | Use | Details |
|---|---|---|---|---|
| $F_1$ | 1 MHz | Working frequency | Emission of the ultrasounds towards the tissue | chosen in the useful frequency band of the transducer 12 |
| $F_2$ | 600 KHz | third monitoring frequency or leakage current monitoring frequency | Detection of fault in the connection chamber | If presence of liquid in the connection chamber (low parasitic resistance, the transducer does not consume at this frequency, the consumption is due to the low parasitic resistance) |
| $F_3$ | 850 KHz | first monitoring frequency | Detection of transducer presence; electrical connection | The transducer resonates in air and water regardless of the air or tissue coupling (before or once implanted) |
| $F_4$ | 960 kHz to 1 MHz | Gas monitoring frequency | Detection of acoustic coupling | The impedance seen by the control unit is distinct depending on whether the transducer is coupled to gas or tissue (only under TX1) |
| $F_0$ | 0 (continuous) | DC voltage | Test of the transducer | a) Transducer dead short circuit (zero impedance, when the transducer is activated) b) Detection of fault in the connection chamber (impedance too low if presence of liquid), completes test at F2 |

The reader will appreciate that the frequencies and thresholds used for the estimation of the quality of the acoustic coupling and for the detection of an operating fault of a transducer can:
- be identical for all ultrasonic devices, or
- be individualized for each ultrasonic device.

This individualization allows taking into account any existing variations between the performances of the different transducers, variations which can be linked to the tolerances of manufacture of the transducers (variations in the surface roughness or in the thickness of each transducer, etc.).

5. Conclusions

The method described above allows assessing the quality of the acoustic coupling between the ultrasonic device and the tissue to be treated. It also allows detecting any operating fault of a transducer.

It is thus possible to limit the risks of ineffectiveness in the treatment linked for example:

to a gas bubble between one (or more) transducer(s) and the tissue to be treated, and/or to a short circuit in the ultrasonic device due to a liquid leakage at its connection terminal.

The detection of such faults allows warning the practitioner so that he can implement solutions for correcting these faults.

The reader will have understood that many modifications can be made to the invention described above without materially departing from the new teachings and advantages described here.

Accordingly, all modifications of this type are intended to be incorporated within the scope of the appended claims.

The invention claimed is:

1. An apparatus for treating a pathology comprising:
   an ultrasonic device including at least one transducer configured to generate ultrasonic waves, the at least one transducer having a front face facing a target medium,
   a remote control unit configured to determine and monitor operating parameters of the ultrasonic device, and to supply said ultrasonic device with electricity during at least one treatment cycle, wherein each treatment cycle is preceded by a wait cycle, and
   electrical connection means between the ultrasonic device and the control unit,
   wherein the control unit is programmed to implement an estimation phase of the quality of an acoustic coupling between the ultrasonic device and the target medium, said estimation phase comprising:
   the emission, by the control unit, of at least one monitoring signal, each monitoring signal having a respective frequency, the measurement, by the control unit, of at least one reflected signal, each reflected signal corresponding to a respective monitoring signal, and the processing of the reflected signal to detect:
either the presence of a liquid in the ultrasonic device, or the presence of a reflective material, such as a gas bubble, between the at least one transducer and the target medium.

2. The apparatus according to claim 1, wherein the estimation phase comprises a step of detecting the presence of liquid in the ultrasonic device, said step including the following sub-steps:
the emission, by the control unit, of a leakage current monitoring signal at a leakage current monitoring frequency,
the measurement, by the control unit, of a reflected leakage current monitoring signal corresponding to the portion of the leakage current monitoring signal that has not been absorbed by the ultrasonic device,
the processing of the reflected leakage current monitoring signal to detect the presence of a liquid in the ultrasonic device.

3. The apparatus according to claim 2, wherein the leakage current monitoring frequency is a frequency that does not belong to an operating frequency range of the at least one transducer.

4. The apparatus according to claim 1, wherein the estimation phase comprises a step of detecting the presence of a gas bubble, said step including the following sub-steps:
the emission, by the control unit, of a gas monitoring signal at a gas monitoring frequency,
the measurement, by the control unit, of a reflected gas monitoring signal corresponding to the portion of the gas monitoring signal that has not been absorbed by the ultrasonic device,
the processing of the reflected gas monitoring signal to detect the presence of a gas bubble between the at least one transducer and the target medium.

5. The apparatus according to claim 4, wherein the gas bubble monitoring frequency is a frequency that belongs an operating frequency range of the at least one transducer.

6. The apparatus according to claim 4, wherein the step of detecting the presence of a gas bubble is implemented for each transducer for at least one wait cycle, said step further including the steps consisting in:
activating each transducer for which no gas bubble has been detected, wherein the activated transducers are supplied with electrical energy for the generation of ultrasonic treatment waves during at least one treatment cycle subsequent to said at least one wait cycle,
deactivating each transducer for which a gas bubble has been detected, wherein the deactivated transducers are not supplied with electrical energy during the treatment cycle subsequent to said at least one wait cycle.

7. The treatment-apparatus according to claim 1, wherein each treatment session comprises a plurality of treatment cycles during which the device emits ultrasonic treatment waves towards a tissue to be treated, each treatment cycle being preceded by a wait cycle, and wherein the control unit is programmed to implement:
the step of detecting the presence of a gas bubble during each wait cycle,
the step of detecting the presence of a liquid during each treatment cycle.

8. The apparatus according to claim 2, wherein the steps of detecting the presence of liquid and gas are implemented sequentially, and wherein the step of detecting the presence of liquid is implemented subsequently to the step of detecting the presence of a gas bubble.

9. The apparatus according to claim 1, wherein the ultrasonic device includes a casing in which each transducer is housed, the casing including a bottom facing the front face of each transducer, the bottom being made of Poly-Ether-Ether-Ketone, and wherein the thickness of the bottom is comprised between 0.3 mm and 0.8 mm, for a working frequency of the transducer equal to 1 MHz.

10. The apparatus according to claim 1, includes an electronic card on which each transducer is electrically connected, and wherein the control unit is further programmed to implement a detection phase of an operating fault of each transducer of the ultrasonic device, said detection phase comprising:
the emission, by the control unit, of at least one test signal having a zero frequency,
the measurement, by the control unit, of at least one reflected test signal,
the processing of the reflected test signal to detect:
either a short circuit between the electronic card and a transducer,
or an electrical connection fault between the electronic card and a transducer.

11. An apparatus for treating a pathology comprising: an ultrasonic device including an electronic card and at least one transducer electrically connected to the electronic card, the at least one transducer being configured to generate ultrasonic waves,
a remote control unit for determining and monitoring operating parameters of the ultrasonic device, and supplying said ultrasonic device with electricity during at least one treatment cycle, each treatment cycle being preceded by a wait cycle,
electrical connection means between the ultrasonic device and the control unit, wherein the control unit is programmed to implement a detection phase of an operating fault of each transducer of the ultrasonic device, said detection phase comprising:
the emission, by the control unit, of at least one test signal, each monitoring signal having a zero frequency,
the measurement, by the control unit, of at least one reflected test signal,
the processing of the reflected test signal to detect:
either a short circuit in the ultrasonic device,
or an electrical connection fault between said and at least one transducer and the electronic card.

12. The apparatus according to claim 11, wherein each treatment session comprises a plurality of treatment cycles during which the ultrasonic device emits ultrasonic treatment waves towards a tissue to be treated, each treatment cycle being preceded by a wait cycle, and wherein the control unit is programmed to implement the step of detecting an operating fault during each wait cycle.

13. The apparatus according to claim 11, wherein the control unit is programmed to implement the step of detecting an operating fault successively for each transducer of the ultrasonic device.

14. The apparatus according to claim 11, wherein each transducer has a front face facing a target medium, and wherein the control unit is further programmed to implement an estimation phase of the quality of an acoustic coupling between the ultrasonic device and the target medium, said estimation phase comprising:
the emission, by the control unit, of at least one monitoring signal, each monitoring signal having a respective frequency, the measurement, by the control unit, of at least one reflected signal, each reflected signal corresponding to a respective monitoring signal, the processing of the reflected signal to detect:
either the presence of a liquid in the ultrasonic device,
or the presence of a reflective material, such as a gas bubble, between said at least one transducer and the target medium.

15. The apparatus according to claim 3, wherein the leakage current monitoring frequency is about 600 kHz for a transducer whose working frequency is equal to 1 MHz.

16. The apparatus according to claim 5, wherein the gas bubble monitoring frequency is a frequency greater than 90% of a working frequency of the at least one transducer.

17. The apparatus according to claim 16, wherein the gas bubble monitoring frequency is about 962 kHz for a transducer whose working frequency is equal to 1 MHz.

18. The apparatus according to claim 9, wherein the thickness of the bottom is comprised, for a working frequency of the at least one transducer equal to 1 MHz, between 0.3 mm and 0.6 mm.

19. The apparatus according to claim 9, wherein the thickness of the bottom is substantially equal to 0.4 mm±0.05 mm, for a working frequency of the at least one transducer equal to 1 MHz.

\* \* \* \* \*